United States Patent
Malker et al.

(10) Patent No.: US 8,529,459 B2
(45) Date of Patent: Sep. 10, 2013

(54) PROCESSING OF PHOTOPLETHYSMOGRAPHY SIGNALS

(75) Inventors: Richard J. Malker, Gainesville, FL (US); Neil R. Euliano, Gainesville, FL (US); Michael W. Stahl, Jr., Gainesville, FL (US)

(73) Assignees: Convergent Engineering, Inc., Gainesville, FL (US); University of Florida Research Foundation, Inc., Gainesville, FL (US)

( * ) Notice: Subject to any disclaimer, the term of this patent is extended or adjusted under 35 U.S.C. 154(b) by 1205 days.

(21) Appl. No.: 11/835,738

(22) Filed: Aug. 8, 2007

(65) Prior Publication Data

US 2009/0043179 A1 Feb. 12, 2009

(51) Int. Cl.
*A61B 5/02* (2006.01)
*A61B 5/08* (2006.01)

(52) U.S. Cl.
USPC .......................... 600/500; 600/484; 600/529

(58) Field of Classification Search
USPC ............... 600/500–507, 529–543, 310–344
See application file for complete search history.

(56) References Cited

U.S. PATENT DOCUMENTS

| | | | |
|---|---|---|---|
| 5,213,099 A | 5/1993 | Tripp, Jr. | |
| 5,273,036 A | 12/1993 | Kronberg | |
| 5,293,874 A | 3/1994 | Takahashi et al. | |
| 5,337,743 A | 8/1994 | Repperger et al. | |
| 5,490,505 A * | 2/1996 | Diab et al. | 600/323 |
| 5,779,631 A | 7/1998 | Chance | |
| 6,051,997 A * | 4/2000 | Yeung et al. | 327/58 |
| 6,081,735 A | 6/2000 | Diab et al. | |
| 6,157,850 A | 12/2000 | Diab et al. | |
| RE38,476 E | 3/2004 | Diab et al. | |
| 7,171,251 B2 | 1/2007 | Sarussi et al. | |
| 7,785,262 B2 | 8/2010 | Melker | |
| 2002/0128544 A1 | 9/2002 | Diab et al. | |
| 2003/0036685 A1* | 2/2003 | Goodman | 600/300 |
| 2003/0236452 A1 | 12/2003 | Melker et al. | |
| 2004/0097797 A1* | 5/2004 | Porges et al. | 600/322 |
| 2004/0204636 A1 | 10/2004 | Diab et al. | |
| 2004/0236196 A1 | 11/2004 | Diab et al. | |
| 2004/0260186 A1* | 12/2004 | Dekker | 600/483 |
| 2007/0032732 A1 | 2/2007 | Shelley et al. | |

FOREIGN PATENT DOCUMENTS

| | | |
|---|---|---|
| JP | 05-124592 | 5/1993 |
| JP | 63-290542 | 11/1998 |
| JP | 2001-204699 | 7/2001 |
| JP | 2003-024287 | 1/2003 |

OTHER PUBLICATIONS

Ahrens, Thomas and Kim Rutherford, "Essentials of Oxygenation." 1993. Jones and Bartlett Publishers. p. 44.*
Goodman, Philip and Rober Wolken, "Pulmonary/Respiatory Therapy Secrets: 7. Pulse Oximetry." 2001. Hanley & Belfus. p. 34.*
Statutory Invention Registration No. H1039, Tripp et al., Apr. 7, 1992.

(Continued)

*Primary Examiner* — Patricia Mallari
*Assistant Examiner* — Tiffany Weston
(74) *Attorney, Agent, or Firm* — Thomas | Horstemeyer, LLP

(57) ABSTRACT

Disclosed herein are methods and devices of processing photoplethysmography signal information. The methods for processing will allow numerous medical observations and diagnoses from a simple, non-invasive probe.

21 Claims, 4 Drawing Sheets

(56) References Cited

OTHER PUBLICATIONS

Rusch et al., Signal processing methods for pulse oximetry, Computers in Biology and Medicine, vol. 26, No. 2, Mar. 1, 1996, pp. 143-158.

Office Action dated Aug. 27, 2012 in copending U.S. Appl. No. 11/573,418.

International Search Report & Written Opinion for PCT/US2005/28355.

Hertzman, A.B. et al., Distinction between Arterial, Venous and Flow Components in Photoelectric Plethysmography in Man, Amer. Jour. Physiol., 130, 177 (1940).

Hertzman, A.B. et al., Applications of Photoelectric Plethysmography in Peripheral Vascular Disease, Am. Heart J., 20, 850 (1940).

* cited by examiner

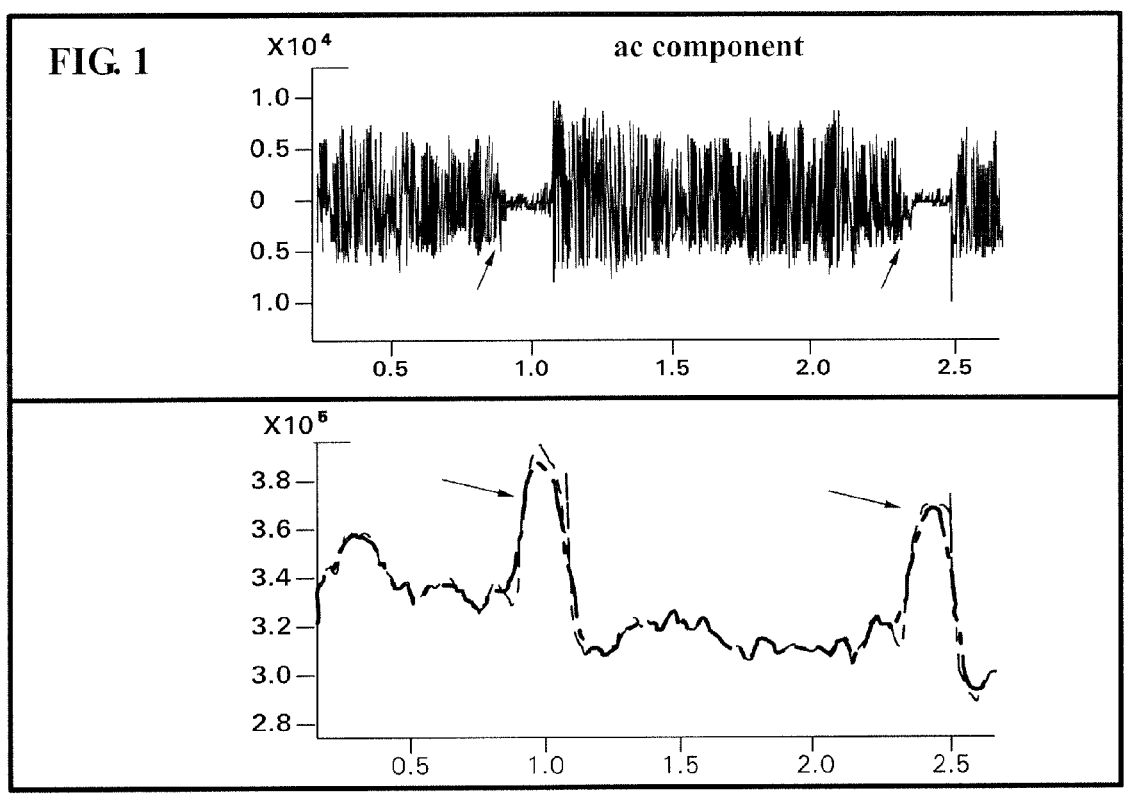

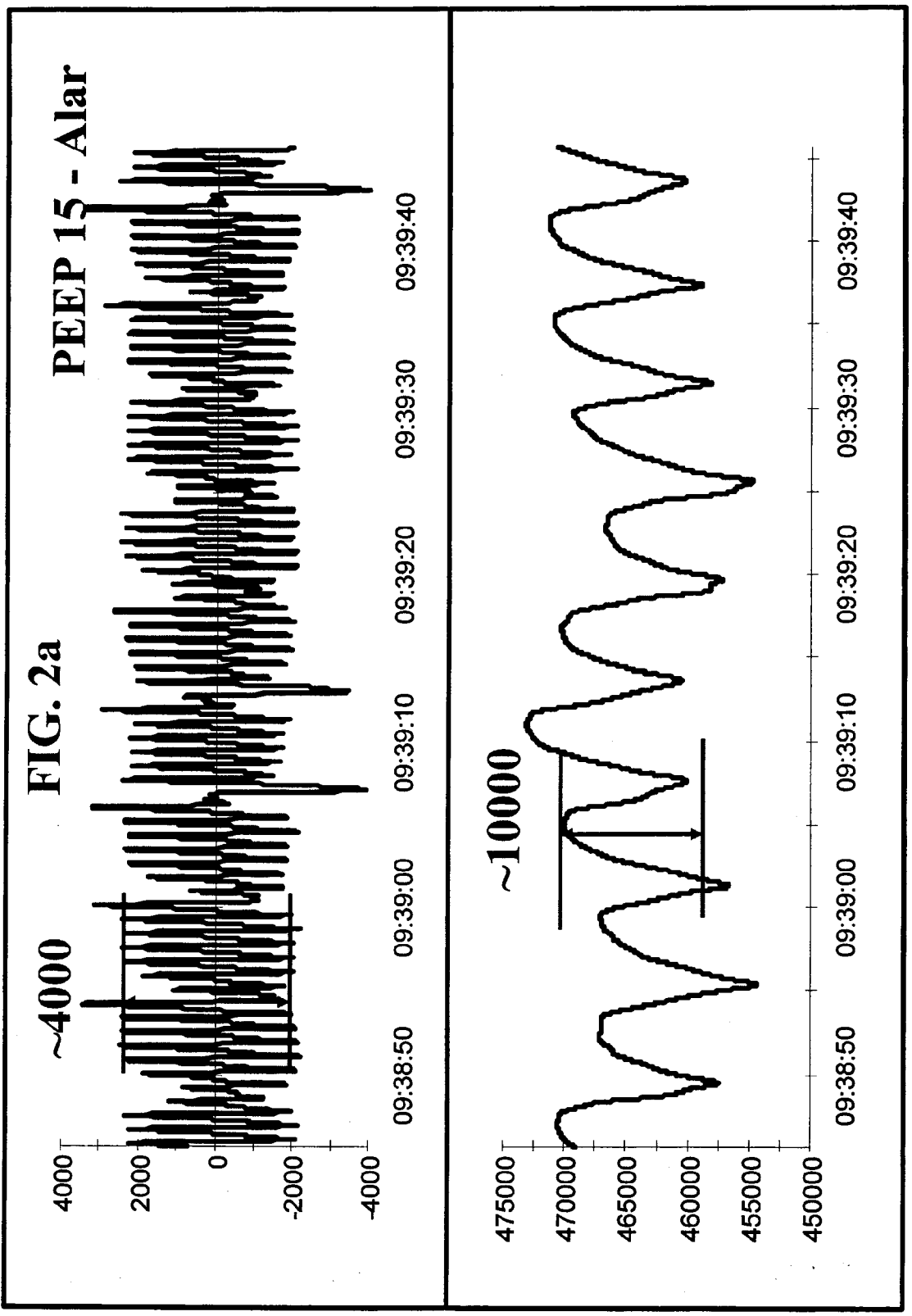

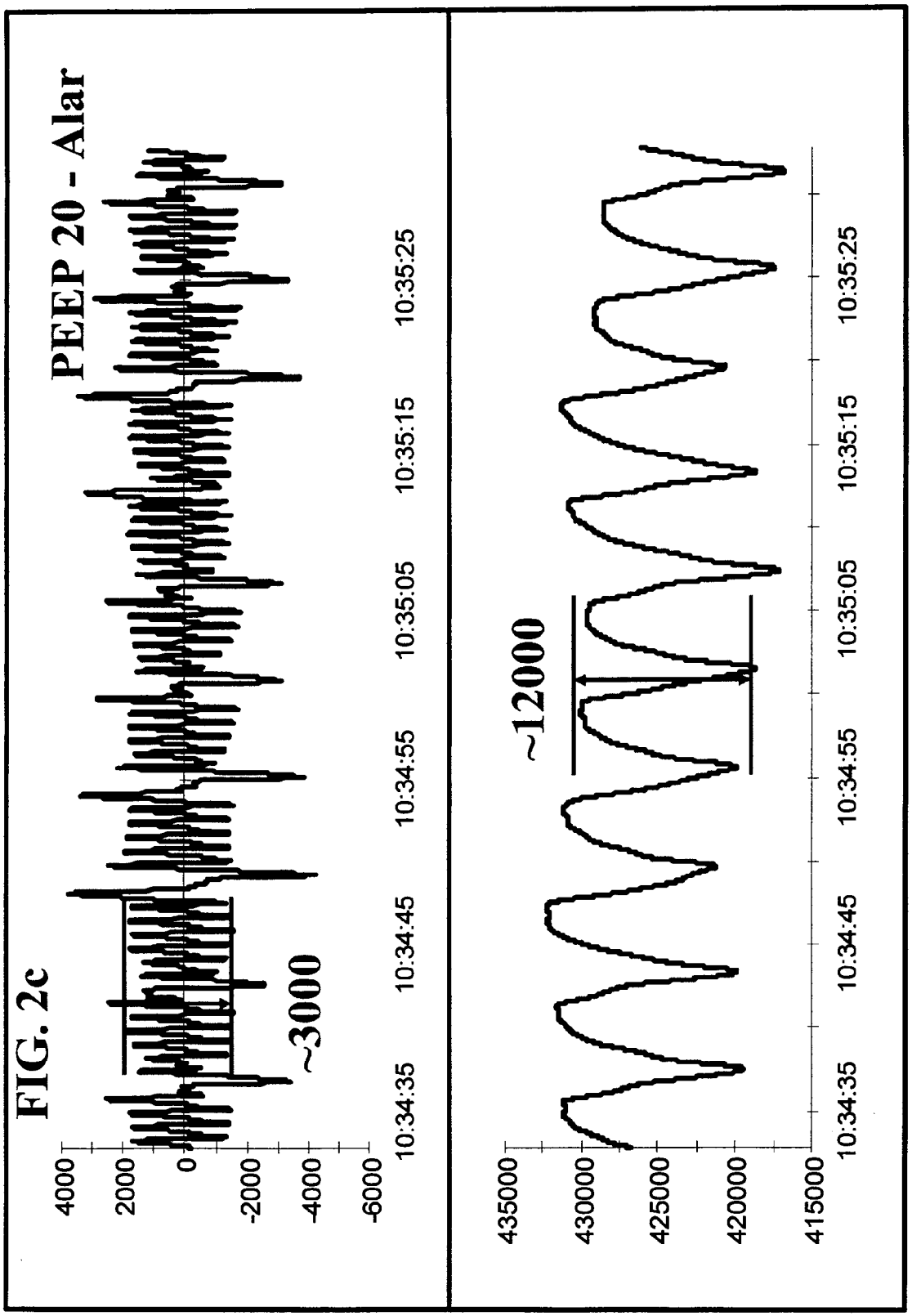

PROCESSING OF PHOTOPLETHYSMOGRAPHY SIGNALS

CROSS-REFERENCE TO RELATED APPLICATIONS

This application is related to and claims the benefit of U.S. patent application Ser. No. 11/573,418 filed Feb. 8, 2007, which is a national stage application stemming from PCT/US05/28355 filed Aug. 10, 2005 and U.S. provisional patent application No. 60/600,548 filed Aug. 11, 2004. The disclosures of the foregoing applications are incorporated herein by reference.

BACKGROUND OF THE INVENTION

In the science of photoplethysmography, light is used to illuminate or trans-illuminate living tissue for the purpose of measuring blood analytes or other hemodynamic or tissue properties. In this monitoring modality light is injected into living tissue and a portion of the light which is not absorbed by the tissues, or scattered in some other direction, is detected a short distance from the entry point. The detected light is converted into an electronic signal that is indicative of the received light signal from the tissue. This electronic signal is then used to calculate physiologic parameters such as arterial blood oxygen saturation and hemodynamic variables such as heart rate, cardiac output, or tissue perfusion. Among the blood analytes that may be measured by photoplethysmography are the various species of hemoglobin, including the percentages of oxyhemoglobin, carboxyhemoglobin, methemoglobin, and reduced hemoglobin in the arterial blood. A device which detects and processes photoplethysmographic signals to measure the levels of various blood analytes and hemodynamic parameters is referred to as a photoplethysmographic apparatus, device, or instrument. Typically these instruments also include, and control, the light sources or emitters used to generate the light that illuminates the tissue. The signals received from the tissue are referred to as photoplethysmographic signals.

The first widespread commercial use of photoplethysmography in medicine was in the pulse oximeter, a device designed to measure arterial blood oxygen saturation. To make these measurements, two different bands of light must be used, with each light band possessing a unique spectral content. Each spectral band, or light band, is typically referred to by the center wavelength, or sometimes by the peak wavelength, of the given band. In pulse oximetry two different light emitting diodes (LEDs) are typically used to generate the sensing light, one with a center, or peak, wavelength near 660 nanometers (nm) and a second with a center, or peak, wavelength near 940 nm.

Light from each LED light source, or emitter, is passed into the tissue-under-test, usually a finger, earlobe, or other relatively thin, well-perfused tissue sample. After passing some distance through the tissue-under-test, a portion of the light not absorbed by the tissue or scattered in some other direction is collected by a photodetector and converted into electronic signals that are directly proportional to the received light signals. The channels, or electronic signals from each of the different light sources, are kept separated through the use of any one of a number of different well-published techniques, including but not limited to, time-division multiplexing or frequency-division multiplexing.

Typically, photoplethysmography is conducted using one pulse oximeter probe. The raw signal stream obtained from a pulse oximeter probe is related to the amount of light from the LED that hits the photodetector of the pulse oximeter probe. The magnitude of the signal from the photodetector is inversely proportional to the amount of absorption of the light between the LED and the photodetector (greater absorption results in less light exciting the photodetector). The absorbed light is due to multiple factors, including absorption due to tissue, absorption due to venous blood, absorption due to arterial blood, and absorption due to the pulsation of arterial blood with each heart beat. Typically, the raw signal from the photodetector is processed (e.g. removal of artifacts and auto-gain of the signal) in order to obtain an arterial oxygen saturation value and the plethysmograph is largely ignored. While some attempts have been made to process photoplethysmography signals, these attempts have focused on the 'cleaning' of signal for purposes of removing motion artifacts. The issue of identifying unique and helpful information that might be included in the photoplethysmography stream has been left largely unexplored.

SUMMARY OF THE INVENTION

Described herein are methods and other embodiments related to the processing of photoplethysmography signals. One aspect of the present invention pertains to a method of isolating an AC and DC component from a stream of plethysmography signals. In addition, the present invention also describes how a respiratory component (RC) is extracted from the DC component. As the AC component and DC component can have different meanings in the art, the AC component will also be referred to herein as the "pulsatile arterial" component, and the DC component will also be referred to herein as the "venous impedance" component. Thus, the term AC component is used to describe a component of a processed plethysmographic signal that represents the pulsatile blood flow that is present in the vascular bed being monitored. The DC component, as used herein, is a phasic slower frequency signal that represents the venous impedance of blood in the vascular bed being monitored and is driven by variations in two phenomena, namely intrathoracic pressure and venous blood volume. One aspect of the invention parses the DC component into these two novel and physiologically meaningful signals. This approach offers a new, non-invasive gauge of respiratory effort. The pulsatile arterial signal has been typically called the plethysmograph and the venous impedance component overlooked, although it is present in the signal and can be isolated as is described herein. A further distinction must be made between the term "DC component" and the term "DC offset". The usage of the term DC component has been described above. The term "DC offset" refers to the amount that the plethysmographic signal is shifted from a baseline that would be present if no light excited the photodiode. The plethysmographic signal is small relative to the magnitude of the DC offset, and "rides" on the DC offset signal. The DC offset varies with the intensity of the LEDS and the amount of light absorbed by the tissues. Thus, if the light path through tissue remains constant, the DC offset increases with increasing LED power, and decreased with less LED power. Alternatively, the DC offset increases as the path of light through the tissues decreases and decreases as the path of light through the tissues increases. Manufacturers usually have circuits built into the pulse oximeter to keep the LED power in a range in which the DC offset will be an adequate signal to discern the photoplethysmograph, but less than that which will oversaturate the photodiode.

In one embodiment, the method pertains to separating out an AC and DC component from a photoplethysmography signal stream. The method comprises identifying the peaks and troughs of said plethysmography signals optionally employing signal processing techniques to further identify and classify the AC signal based on its characteristic shape (presence of a dicrotic notch, etc); identifying a common point, such as the midpoint, minimum or maximum, or some other point values between said peaks and troughs, wherein the interpolated line connecting said common point values represents said DC component; extracting said DC component from said plethysmography signals, thereby separately obtaining said AC component, whereby an AC component and DC component are individually isolated. This and other advantageous aspects will be described herein.

In another embodiment, the method pertains to separation of respiratory component (RC) from the DC component. This separation can be achieved in several ways. An algorithm identical in nature to one described above to parse the AC component can be used. This is true because after the AC has been removed, the RC is the component with the next highest average frequency. In other words, the highest frequency peaks and troughs of the DC component are due to respiratory effort. Sophisticated feature detection and pattern recognition routines can be employed to further identify peaks and troughs that match the characteristic shape of breathing. In addition to this novel algorithm, traditional means such as band-pass filtering can be used to generate an RC component.

In another embodiment, both the infrared and RED plethysmograms are used to improve the accuracy of AC, RC, and DC separation. Other LED wavelengths may also be employed. Regions where the signals from different wavelengths differ, can be isolated and the discrepancies can be corrected. Such an approach has a higher signal-to-noise and is more robust than using a single LED wavelength.

BRIEF DESCRIPTION OF THE DRAWINGS

FIG. 1 represents a plethysmograph from a pulse oximeter probe positioned on the cheek. The AC component (or cardiac component for purposes of this example) is provided on the top and the DC offset (or non-cardiac component for purposes of this example) is provided on the bottom. Pressing on the carotid diminishes blood flow, as seen in the AC component (see arrow). Conversely, the DC offset goes up when the carotid is depressed (see arrows).

FIG. 2 represents a plethysmograph obtained from a nasal alar of a patient undergoing PEEP therapy during mechanical ventilation with spontaneous breathing. FIG. 2a, shows the plethysmograph (AC and DC components) while the patient is undergoing 15 cm/H2O of PEEP. FIG. 2c shows the plethysmograph when the PEEP is increased to 20 cm/H2O.

DETAILED DESCRIPTION

Figure 2B:
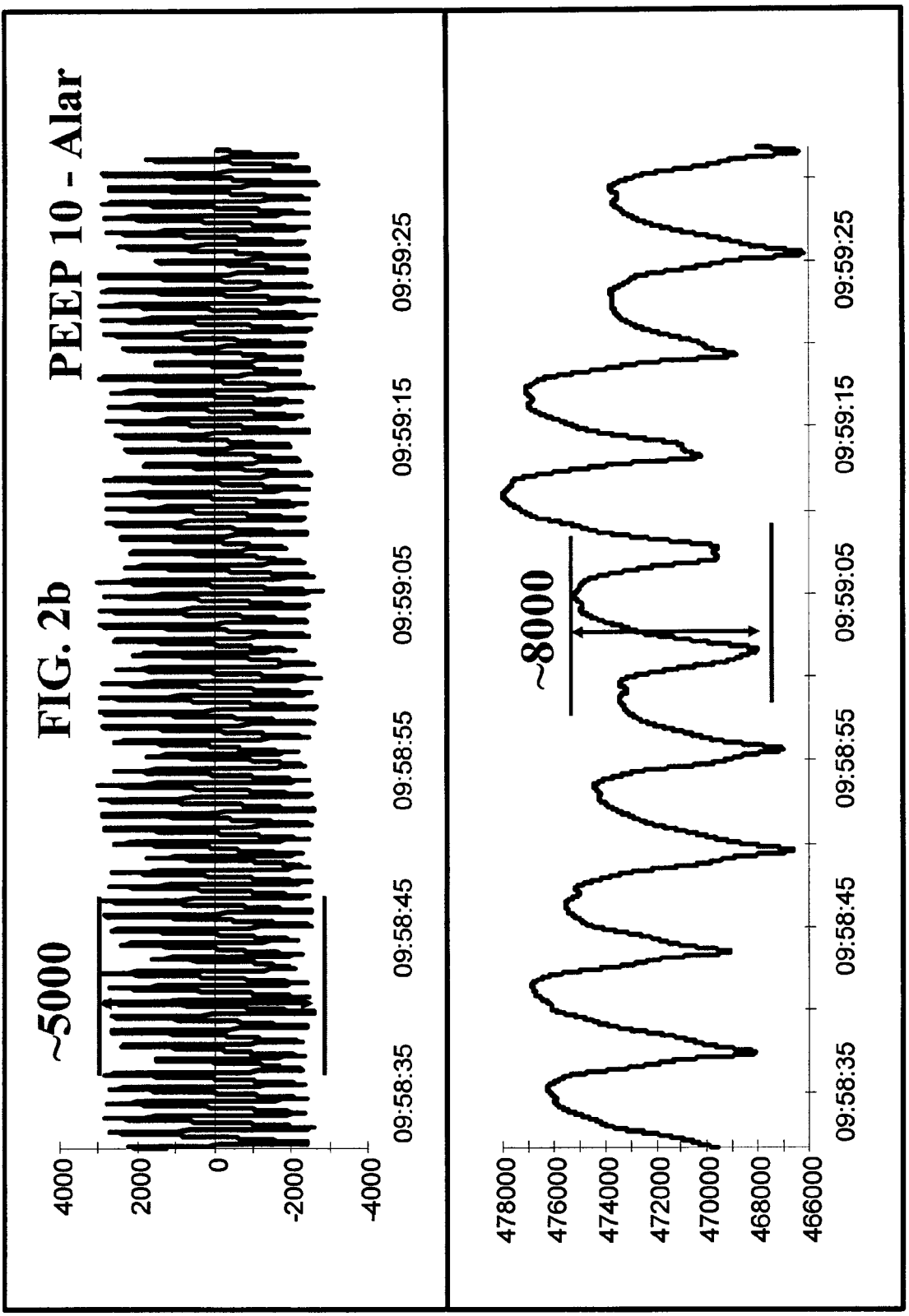
FIG. 2b shows the plethysmograph when the PEEP is dropped to 10 cm/H2O.

The inventors have developed a new processing of the plethysmography signal such that important information may be extrapolated from the signal. This novel processing reveals information not before realized to be obtainable from a plethysmography signal stream. In the past, the plethysmography signal stream was typically obtained from a peripheral site such as the finger, or other extremity. It is the inventors' belief that obtaining the plethysmograph from a central site lacks much of the background noise found in the plethysmograph from a peripheral site, and it is the obtainment of this "less noisy" signal that eventually led to the realization that information such as respiration rate and venous capacitance can be extrapolated.

The raw signal stream obtained from a pulse-oximeter probe is related to the amount of light from the LED that hits the photodetector of the pulse-oximeter probe. The magnitude of the signal from the photodetector is inversely proportional to the amount of absorption of the light between the LED and the photodetector (greater absorption results in less light exciting the photodetector). The absorbed light is due to multiple factors, including absorption due to tissue, absorption due to venous blood, absorption due to arterial blood, and absorption due to the pulsation of arterial blood with each heart beat. Typically, the raw signal from the photodetector is processed (e.g. removal of artifacts and autogain of the signal) and also separated into two components. The two components are intended to be the time varying signals that are related to the beat-to-beat variations caused by the pulsation and flow of blood in the arteries (typically called the AC component), and the slowly varying components that is related to the other physiologic and physical properties of the signal, typically called the DC component (including non-pulsatile arterial blood, pulsatile and non-pulsatile venous blood and tissue and bone). The AC signal has been typically called the plethysmography and the DC component overlooked.

The amplitude of the AC component contains information about the amount of arterial blood flowing past the detector. In order to correctly interpret this information, the AC and DC components must be separated more rigorously than in standard monitors. In particular, the pulsatile arterial component should contain only that information that relates to beat-to-beat variations of the heart. The DC component should contain the other, lower frequency effects from physiology such as the respiratory effects, blood pooling, venous impedance, sympathetic and parasympathetic tone, etc. and physical sensor changes (e.g. changes in the orientation of the probe, etc.).

According to one signal processing method embodiment of the subject invention, the effects of the individual heart beats in the plethysmograph is separated out from the other information, which is fundamentally a slightly different goal than conventional processing, which is basically to obtain an adequate AC component and discarding all other information. Standard practice is to implement a DC removal technique that involves removing the DC component by a low pass filter. This technique, however, does not sufficiently separate (phasic pulsatile arterial flow information) from the other sources of information. The subject processing method obtains higher fidelity separation of signals, which is critical when dealing with precise measurements of variables. In a specific embodiment, the high fidelity AC component and the DC component of the plethysmography signal (previously ignored by those in the art) are achieved by:

1) discretely picking the dominant peaks and troughs of the signal (improved noise/artifact rejection can be achieved by looking for peaks and troughs that exist at the expected heart rate, estimated by Fourier or autocorrelation analysis, or from past data)

2) finding a common point between peaks and troughs 3) extracting the DC component as the interpolated (and possibly smoothed or splined) line that connects these common points 4) extracting the AC component as the raw signal minus the DC component.

Similarly, finding the dominant peaks or troughs (also referred to herein as extrema) of the signal and interpolating between these points will also suffice to implement this separation. The AC component is extracted as the raw signal minus the interpolation between minima or maxima.

Furthermore, directly identifying any common point in the cardiac component and interpolating between these points may also implement this separation. For example, in addition to finding midpoints, minimum points, or maximum points, locating the zero crossing point, inflection point, dicrotic notch (or waveforms from reflected pressure waves), or position that subtends coequal positive and negative areas may be implemented.

Additionally, information about the shape of the cardiac or respiratory waveforms (cardiac signal is more triangular and respiratory more sinusoidal) can be used to separate the two signals or improve the performance of the algorithm above. For example, an adaptive filter can be used to find the frequency that most closely matches the signal shape expected to correspond to the cardiac or respiratory waveform. This frequency can then be used for the peak/trough analysis, or can be used via standard filtering methods to extract the desired signal.

The AC and DC components, as described herein, are intended to be the time varying signals that are related to the beat-to-beat variations caused by the pulsation and therefore, when recorded over time, the flow of blood in the arteries (the AC component, although different from the AC component described by others), and the slowly varying components that are related to the other physiologic and physical properties of the signal related to the impedance of the venous vessels and the changes in intrathoracic pressure, the venous (DC) component which differs from the "classical" description of the DC component which is said to include non-pulsatile arterial blood, pulsatile and non-pulsatile venous blood and tissue and bone. The amplitude and area under the curve (AUC) of the AC component contains information about the amount of arterial blood flowing past the detector. In order to correctly interpret this information, the AC and DC components must be separated more rigorously than with the algorithms in standard monitors and previously described in the literature. In particular, the pulsatile arterial component should contain only that information that relates to beat-to-beat variations of the heart. The DC component should contain lower frequency effects from physiology (such as the respiratory effects, blood pooling, venous impedance, etc.) and physical sensor changes (e.g. changes in the orientation of the probe, etc.).

Accordingly, the inventors have discovered and characterized for the first time at least three separate components of the plethysmograph signal: (a) blood pulsation signal, (b) time-varying DC signals including respiratory rate signals and other low frequency signals (e.g., physiological changes due to parasympathetic and sympathetic nervous systems), and (c) the classical DC component signal which is a function of the tissue (muscle, bone, etc) at the probe site, and is the baseline DC component on which the venous impedance signal rides.

Pulse oximeter probes useful in accordance with the teachings herein include, but are not limited to, those described in co-pending U.S. application Ser. Nos. 10/176,310; 10/751,308; 10/749,471; and 60/600,548, the disclosures of which are all incorporated herein in their entirety.

As referred to above, the DC offset (component) of the plethysmogram is an indicator of venous impedance, while the arterial component is a measure of regional blood flow. During forced airway maneuvers, intrathoracic pressure changes dramatically. These pressure changes are transmitted directly to the veins in the head, because there are no anatomical valves in veins leading to the head. Changes in intrathoracic pressure have direct effects on both the beat to beat pulsatile arterial blood flow (AC component) and the amount of venous blood in the vascular bed being monitored on a breath to breath basis. These effects are present even during quiet breathing, but are far more pronounced with "airway maneuvers" such as the Valsalva and Mueller maneuvers, and during exacerbation of respiratory conditions which increase airway resistance and/or decrease lung compliance. These pronounced changes are often referred to as "pulsus paradoxus" when measured by arterial blood pressure or direct arterial blood monitoring. All conditions which affect airway resistance (increase) and lung compliance (decreased) increase the respiratory muscle work (work of breathing for each breath). As the work of breathing increases, there are wider swings in intrathoracic pressure which in turn lead to phasic variations in pulsatile arterial blood flow and venous impedance. In view of the teachings herein, respiratory rate can be easily determined when monitoring at "central source sites" and the degree of change in both the AC and DC components are proportional to the degree of airway obstruction and/or lung compliance. At a given level of resistance and or compliance, variations in the amplitude and AUC of both components can also be an indication of volume status. Thus, a plethora of information on both respiratory and cardiopulmonary mechanics can be ascertained from the processed plethysmograph, especially when it is obtained from a "central source site".

EXAMPLES

FIG. 1 represents a plethysmograph from a pulse oximeter probe positioned on the cheek. The AC component is provided on the top and the DC component is provided on the bottom. Pressing on the carotid diminishes blood flow, as seen in the AC component (see arrow). Conversely, the DC component goes up when the carotid is depressed (see arrows). This confirms the inventors' beliefs of the physiological phenomenon that is represented in the DC component. That is, for this example, the DC component increasing demonstrates that there is both less blood flowing to the cheek, and because only the artery is occluded but not venous return there is low venous impedance. The effect is that less blood is flowing to the cheek, but that blood is able to leave the veins in the cheek and return to the chest. Since there is less blood between the LED and photodetector, there is less absorption of the signal, resulting in a higher DC component signal. By separating the AC and DC components, the effects on arterial blood flow and venous return can both be evaluated, which enables several important medical observations.

FIG. 2a-c represents plethysmographs from a patient in the ICU on a ventilator. The patient has a probe which is located at the nasal alar. In FIG. 2a, the patient is undergoing 15 cm/H2O of PEEP during mechanical ventilation with spontaneous breathing. At this treatment, the AC amplitude is ~4,000 and the DC ~10,000. When the PEEP is dropped to 10 cm/H2O (shown in FIG. 2b), the AC amplitude increases to 5,000 and the DC decreases to 8,000 indicating better perfusion and less venous impedance (less blood trapped in the head due to high intrathoracic pressure and larger arterial—venous pressure gradient).

In FIG. 2c, there is a dramatic change exhibited when the PEEP is increased to 20 cm/H2O. The AC decreases to 3,000 indicated marked decrease in arterial perfusion, and the DC increases to 12,000 indicating that more blood is trapped in the head and not returning to the chest (decreased arterial—venous pressure gradient). The net effect is decreased perfusion in the local vascular bed and presumably to the brain as well.

Computer Related Implementation

The term "processing module" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory device. The memory device may be a single memory device or a plurality of memory devices. Such a memory device may be a read-only memory, random access memory, volatile memory, non-volatile memory, static memory, dynamic memory, flash memory, and/or any device that stores digital information.

As will be appreciated by one of skill in the art, embodiments of the present invention may be embodied as a device, method, or system comprising a processing module, and/or computer program product comprising at least one program code module. Accordingly, the present invention may take the form of an entirely hardware embodiment or an embodiment combining software and hardware aspects. Furthermore, the present invention may include a computer program product on a computer-usable storage medium having computer-usable program code means embodied in the medium. Any suitable computer readable medium may be utilized including hard disks, CD-ROMs, DVDs, optical storage devices, or magnetic storage devices.

The computer-usable or computer-readable medium may be or include, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of certain embodiments of the present invention may be written in an object oriented and/or conventional procedural programming languages including, but not limited to, Java, Smalltalk, Perl, Python, Ruby, Lisp, PHP, "C", FORTRAN, or C++. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Certain embodiments of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer-readable program code modules. These program code modules may be provided to a processing module of a general purpose computer, special purpose computer, embedded processor or other programmable data processing apparatus to produce a machine, such that the program code modules, which execute via the processing module of the computer or other programmable data processing apparatus, create means for implementing the functions specified in the flowchart and/or block diagram block or blocks.

These computer program code modules may also be stored in a computer-readable memory that can direct a computer or other programmable data processing apparatus to function in a particular manner, such that the program code modules stored in the computer-readable memory produce an article of manufacture.

The computer program code modules may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference to the extent they are not inconsistent with the teachings herein.

What is claimed is:

1. A method of isolating an AC component signal stream and a DC component signal stream from a raw plethysmography signal stream comprising
    identifying peaks and troughs of said raw plethysmography signal stream using at least one processing device, wherein said peaks and troughs are those that exist at an expected heart rate;
    identifying minimum values or midpoints between said peaks and troughs using said at least one processing device, and
    interpolating between said midpoints or minimum values to define said DC component signal stream; and
    extracting said interpolated DC component signal stream from said raw plethysmography signal stream using said at least one processing device, thereby separately obtaining said AC component signal stream, whereby said AC component signal stream and said DC component signal stream are individually isolated.

2. The method of claim 1 wherein said raw plethysmography signal stream is obtained from an individual by positioning at least one photodetector on said individual's right or left nares; and positioning at least one LED on the individual's right or left nostril just across from said at least one photodetector.

3. The method of claim 2, wherein said at least one photodetector is positioned on top of said individual's fibro-areolar region of said individual's nose.

4. A system for processing plethysmography signals from a patient comprising at least one pulse oximeter probe configured for securing to a central source site of said patient and effective to generate a raw plethysmography signal stream; and a computer connected to and in communication with said at least one pulse oximeter probe, said computer comprising at least one processing module, a first computer-readable program code module configured to cause said computer to process said raw plethysmography signal stream to obtain an AC component signal stream or a DC component signal stream, or both, and a second computer-readable program code module configured to cause said computer to analyze said AC component signal stream or said DC component signal stream, or both, to determine a decrease in amplitude of either said AC component signal stream or DC component signal stream, or both;

wherein said AC component signal stream and said DC component signal stream are isolated from each other from said raw plethysmography signal stream by said first computer-readable program code module causing said computer to identify the peaks and troughs of said plethysmography signal stream that exist at an expected heart rate, to identify minimum values or midpoints between said peaks and troughs, to interpolate between said midpoints or minimum values to define said DC component signal stream, and to extract said interpolated DC component signal stream from said raw plethysmography signal stream, thereby separately obtaining said AC component signal stream, whereby the said AC component signal stream and said DC component signal stream are individually isolated.

5. The system of claim 4, wherein said computer further comprises a display screen.

6. A computer program product for use with a computer comprising at least one processing module, said product comprising:

a non-transitory computer-usable medium comprising computer readable program code modules embodied in said computer-usable medium:

a non-transitory computer readable first program code module configured to cause said computer to process a raw plethysmography signal stream obtained from a pulse oximeter probe by separating out a AC component signal stream and a DC component signal stream, wherein said AC component signal stream and said DC component signal stream are separated from each other from the raw plethysmography signal stream by said non-transitory computer-readable program code module configured to cause said computer to identify peaks and troughs of said raw plethysmography signal stream that exist at an expected heart rate, to identify minimum values or midpoints between said peaks and troughs, to interpolate between said midpoints or minimum values to define said DC component signal stream, and to extract said interpolated DC component signal stream from said raw plethysmography signal signal stream, thereby separately obtaining said AC component signal stream, whereby said AC component signal stream and said DC component signal stream are individually isolated; and a non-transitory computer-readable second program code module for causing said computer to analyze said AC component signal stream or said DC component signal stream, or both, to determine a decrease in amplitude of either said AC component signal stream or said DC component signal stream, or both.

7. A method of obtaining processed photoplethysmography readings from an individual, said method comprising:

obtaining a pulse oximeter probe comprising at least one LED and at least one photodetector;

securing said probe onto said individual's right and/or left nasal alar, whereby tissue of said nasal alar rests between said at least one photodetector and said at least one LED; and monitoring a raw photoplethysmography signal stream generated by said probe responsive to blood flow at said tissue of said nasal alar; and isolating an AC component signal stream and a DC'component signal stream from the raw photoplethysmography signal stream by a method comprising identifying peaks and troughs of said photoplethysmography signal stream, wherein said peaks and troughs are those that exist at an expected heart rate; identifying minimum values or midpoints between said peaks and troughs, interpolating between said midpoints or minimum values to define said DC component signal stream; extracting said interpolated DC component signal stream from said raw plethysmography signal stream, thereby separately obtaining said AC component signal stream, whereby said AC component signal stream and said DC component signal stream are individually isolated.

8. A method of isolating an AC and DC component signal stream from a raw plethysmography signal stream comprising identifying extrema of said raw plethysmography signal stream using at least one processing device, whereby the extrema are those that exist at an expected heart rate;

identifying a common point relative to the extrema using said at least one processing device, interpolating between said common points to define said DC component signal stream; and extracting said interpolated DC component signal stream from said raw plethysmography signal stream using said at least one processing device, thereby separately obtaining said AC component signal stream, whereby said AC component signal stream and said DC component signal stream are individually isolated.

9. The method of claim 8, wherein said common point is a midpoint.

10. The method of claim 8, wherein said common point is a maximum point.

11. The method of claim 8, wherein said common point is a minimum point.

12. The method of claim 8, wherein said common point is a dicrotic notch.

13. The method of claim 8, wherein said common point is a zero-crossing point.

14. The method of claim 8, wherein said common point is an inflection point.

15. The method of claim 8, wherein said common point is a point of equal areas.

16. The method of claim 8, wherein said raw plethysmography signal stream is obtained from a pulse oximeter sensor secured to a nasal alar of a patient.

17. A method of isolating from a raw plethysmography signal stream a high frequency component signal stream, a first low frequency component signal stream and a second low frequency component signal stream, said method comprising identifying extrema of said raw plethysmography signal stream using at least one processing device, wherein said extrema are those that exist at an expected heart rate;

identifying a common point relative to the extrema using at least one processing device, interpolating between said common points to represent a low frequency content of the signal; and extracting said interpolated low frequency content from said raw plethysmography signal stream using said at least one processing device, thereby separating said high frequency component signal stream from said low frequency content.

18. The method of claim 17, wherein said high frequency component signal stream comprises a cardiac component and said low frequency content comprises a respiratory component and a sympathetic and parasympathetic tone component.

19. The method of claim 17, further comprising separating said first low frequency component from said second low frequency component.

20. The method of claim 1, further comprising using said isolated AC component signal stream and/or said DC component signal stream to measure at least one of respiration rate, respiration effort and venous impedance.

21. The method according to claim 1 wherein said time varying raw plethysmography signal stream is acquired from a central source site.

* * * * *

UNITED STATES PATENT AND TRADEMARK OFFICE
CERTIFICATE OF CORRECTION

| | | |
|---|---|---|
| PATENT NO. | : 8,529,459 B2 | Page 1 of 1 |
| APPLICATION NO. | : 11/835738 | |
| DATED | : September 10, 2013 | |
| INVENTOR(S) | : Richard J. Melker | |

It is certified that error appears in the above-identified patent and that said Letters Patent is hereby corrected as shown below:

Title Page, Item (12) "Malker et al" should read -- Melker et al --

Title Page, Item (75) Inventors, first inventor should read -- Richard J. Melker, Gainesville, FL (US) --

Signed and Sealed this
Tenth Day of June, 2014

Michelle K. Lee
*Deputy Director of the United States Patent and Trademark Office*